(12) United States Patent
Yoon et al.

(10) Patent No.: US 11,913,912 B2
(45) Date of Patent: Feb. 27, 2024

(54) HOLE EXPANSION RATIO TESTING DEVICE, HOLE EXPANSION RATIO TESTING METHOD, AND OPERATING PROGRAM

(71) Applicant: INDUSTRY-UNIVERSITY COOPERATION FOUNDATION HANYANG UNIVERSITY ERICA CAMPUS, Ansan-Si (KR)

(72) Inventors: Jonghun Yoon, Ansan-si (KR); Seungho Choi, Ansan-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 444 days.

(21) Appl. No.: 17/203,254

(22) Filed: Mar. 16, 2021

(65) Prior Publication Data

US 2021/0223150 A1 Jul. 22, 2021

Related U.S. Application Data

(63) Continuation of application No. PCT/KR2019/012384, filed on Sep. 24, 2019.

(30) Foreign Application Priority Data

Sep. 27, 2018 (KR) .......................... 10-2018-0115221

(51) Int. Cl.
*G01N 3/06* (2006.01)
*G06T 7/00* (2017.01)
(Continued)

(52) U.S. Cl.
CPC ............... *G01N 3/068* (2013.01); *G01N 3/58* (2013.01); *G01N 33/2045* (2019.01);
(Continued)

(58) Field of Classification Search
CPC ......... G06T 7/11; G06T 7/0004; G06T 7/194; G06T 7/136; G06T 2207/30136;
(Continued)

(56) References Cited

U.S. PATENT DOCUMENTS 8,520,892 B2  8/2013  Kuleschow et al.
2009/0177417 A1*  7/2009  Yonemura ............... G06F 30/15
                                                702/42

FOREIGN PATENT DOCUMENTS

KR  10-2013-0073590 A  7/2013
KR  10-1538696 B1  7/2015
(Continued)

OTHER PUBLICATIONS

Kim Young Suk et al "System and Method for Testing Hole Expansion for Sheet Materials Using Pattern Recognition Technique", May 12, 2016, KR 20160052145A (Year: 2016).*
(Continued)

*Primary Examiner* — Sang H Nguyen
(74) *Attorney, Agent, or Firm* — Sughrue Mion, PLLC

(57) ABSTRACT

Disclosed are a hole expansion ratio testing device, a hole expansion ratio testing method, and an operation program. The hole expansion ratio testing device includes a chucking unit configured to chuck a plate member having a hole, a punching unit inserted into the hole and configured to expand the hole, an image acquisition unit configured to acquire an image of the hole expanded by the punching unit, and an analysis unit configured to extract an interest area corresponding to the hole from the acquired image, linearize the interest area, and provide information on a crack as a blob changes due to the linearization.

13 Claims, 26 Drawing Sheets

(51) Int. Cl.
   *G06T 7/11*       (2017.01)
   *G06T 7/136*      (2017.01)
   *G06T 7/194*      (2017.01)
   *G01N 3/58*       (2006.01)
   *G01N 33/2045*    (2019.01)

(52) U.S. Cl.
   CPC .............. *G06T 7/0004* (2013.01); *G06T 7/11* (2017.01); *G06T 7/136* (2017.01); *G06T 7/194* (2017.01)

(58) Field of Classification Search
   CPC .. G06T 2207/20021; G01N 3/08; G01N 3/58; G01N 3/068; G01N 33/2045; G01N 2203/027; G01N 2203/0647; G01N 2203/0282; G01N 2021/8887; G01N 33/20
   See application file for complete search history.

(56) References Cited

FOREIGN PATENT DOCUMENTS

KR   10-2016-0052145 A   5/2016
KR   10-2018-0072401 A   6/2018

OTHER PUBLICATIONS

Kim Hong Han et al "System and Method for Hole Expansion Test", Jun. 29, 2018, KR 20180072401A. (Year: 2018).*
International Search Report of PCT/KR2019/012384 dated Jan. 2, 2020 [PCT/ISA/210].

* cited by examiner

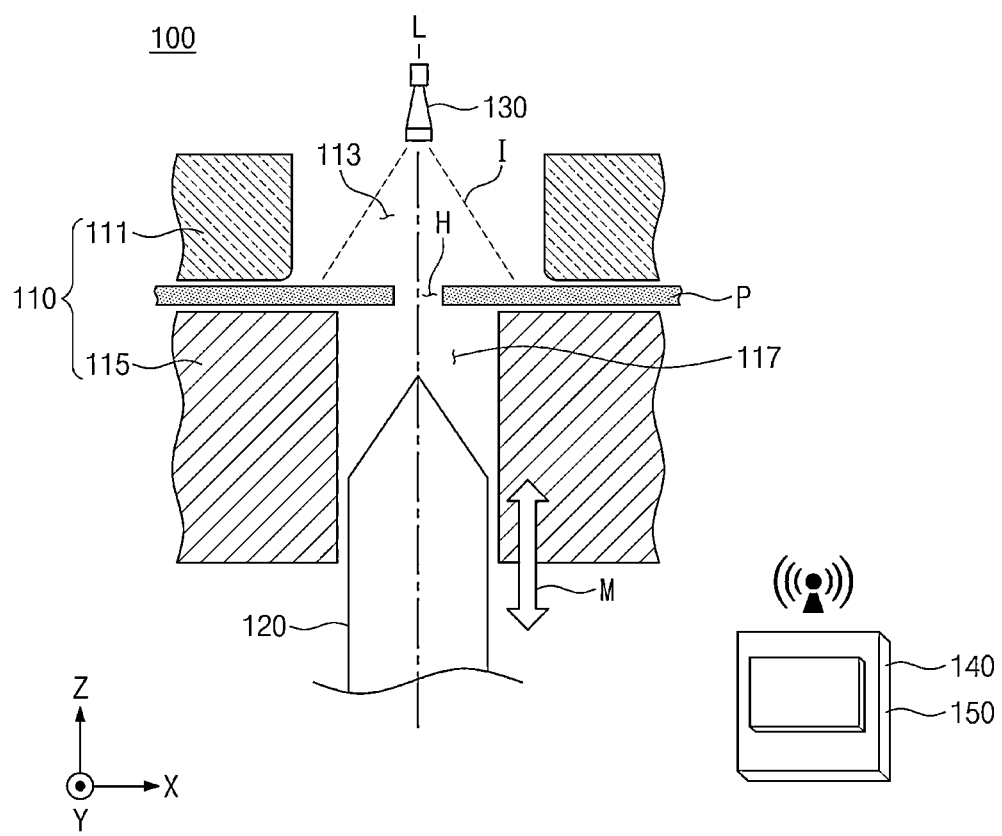
[Fig. 1]

[Fig. 2]
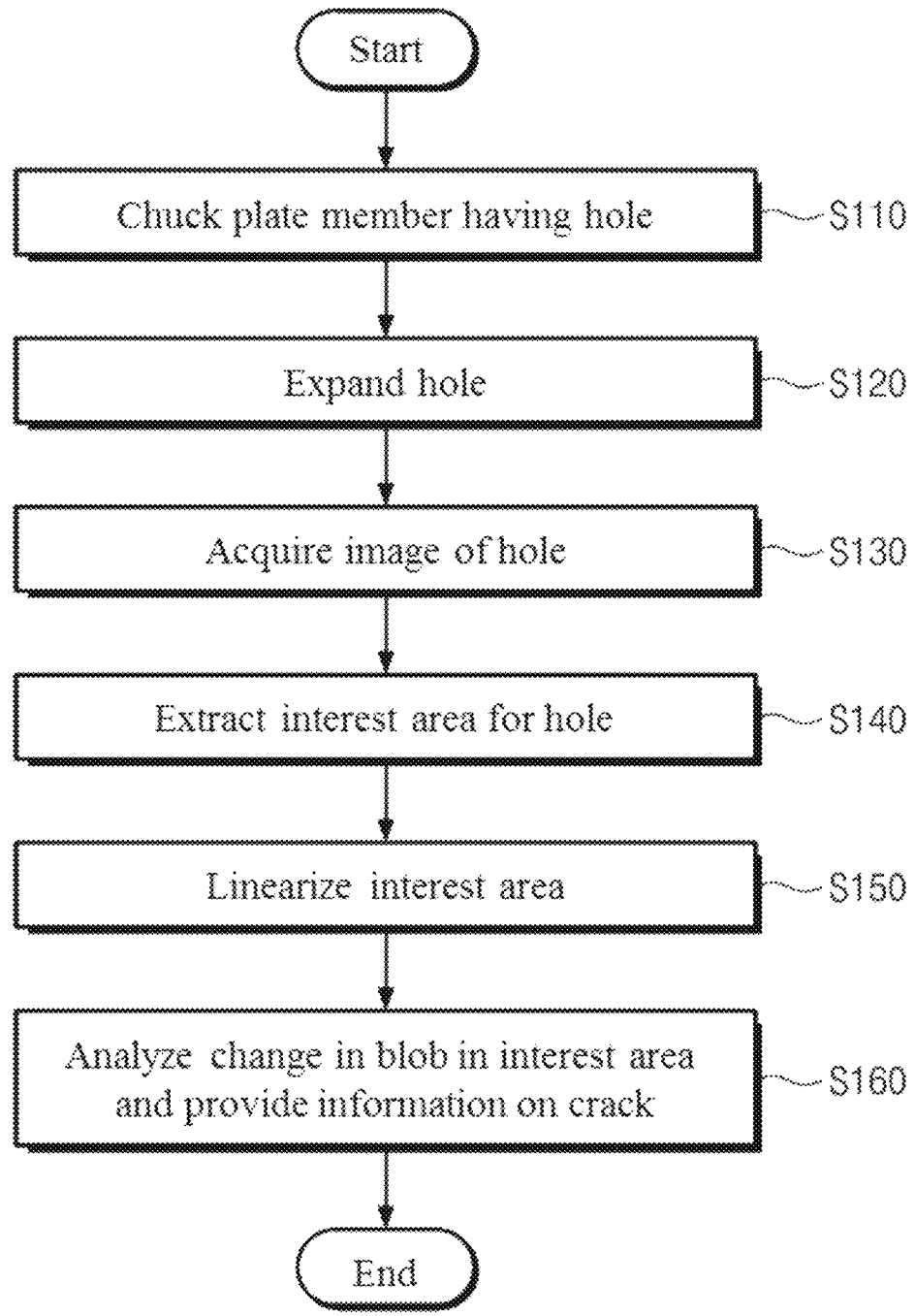

[Fig. 3]
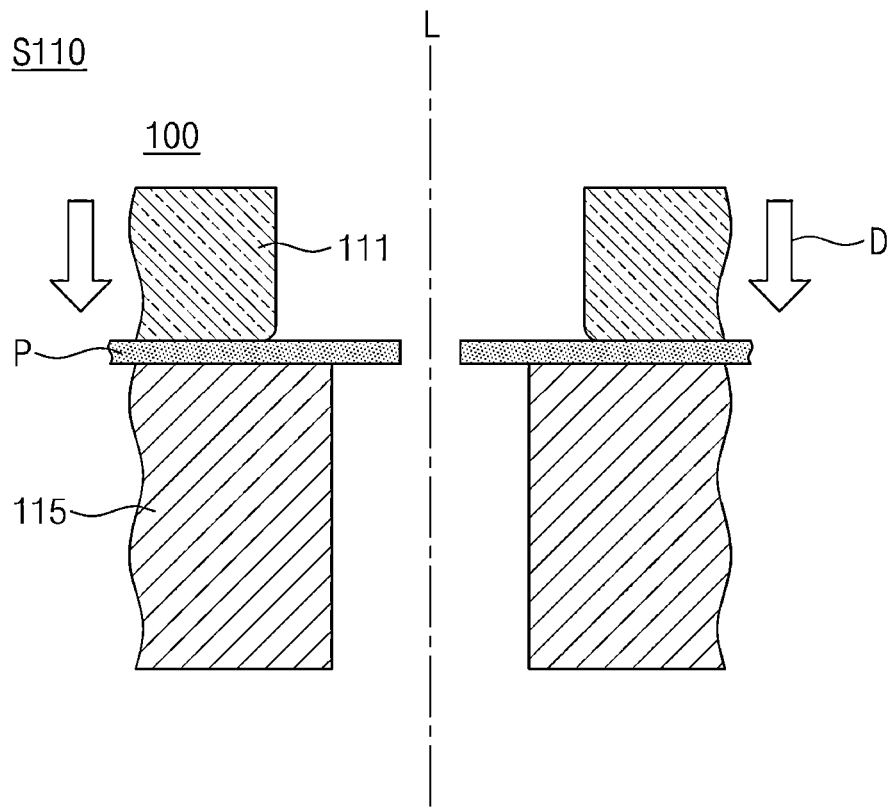

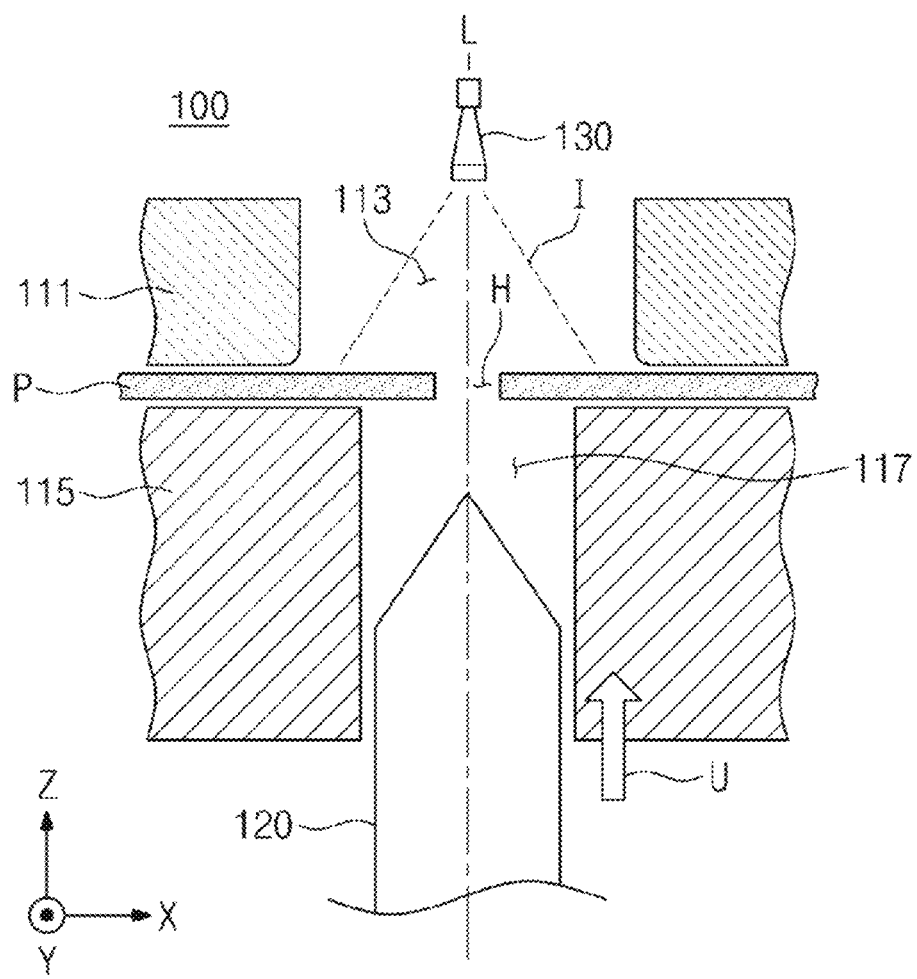

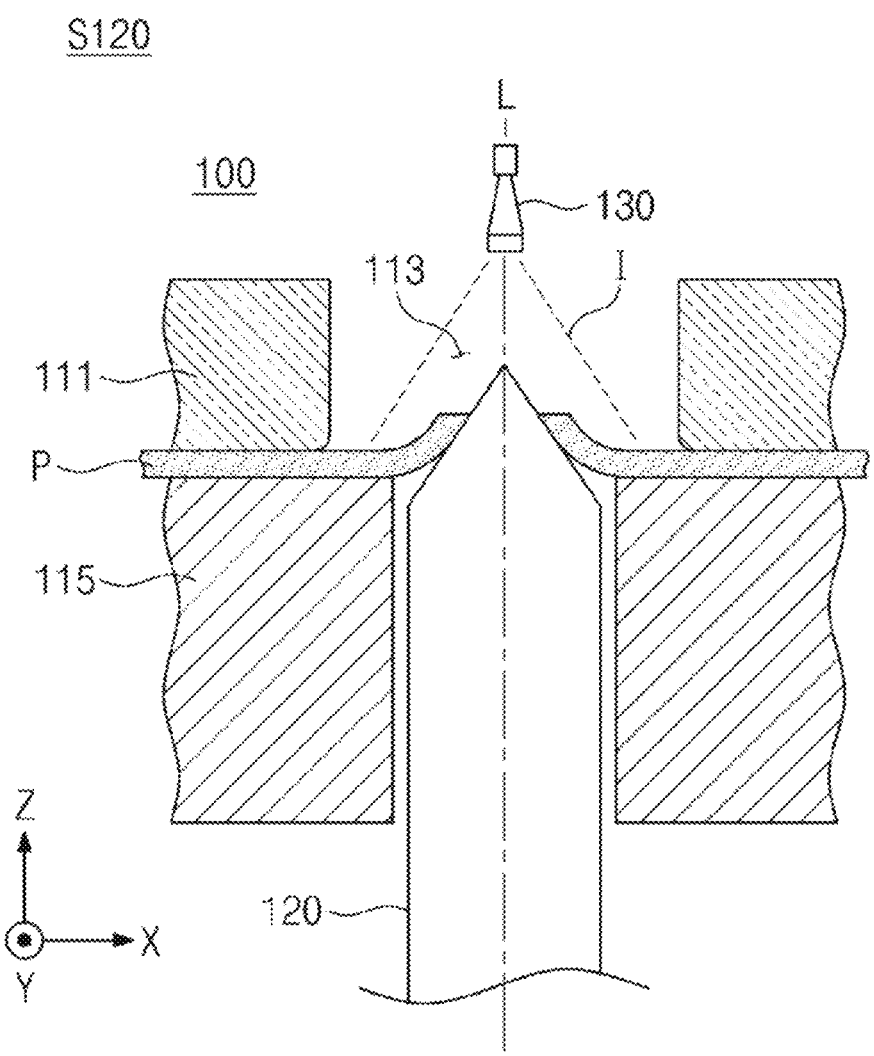

[Fig. 5]
S130
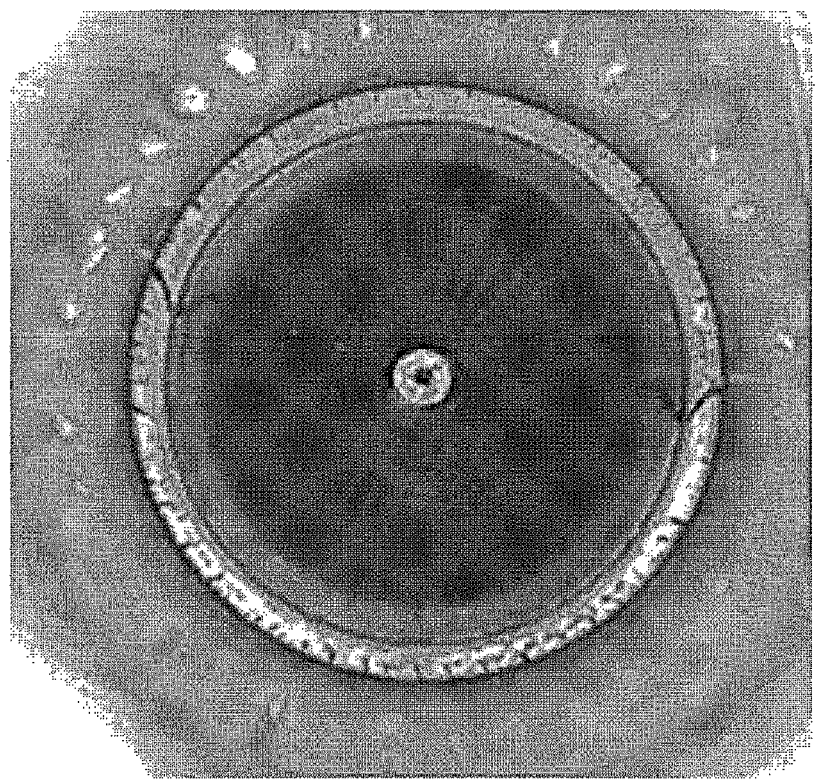

[Fig. 6]
S140
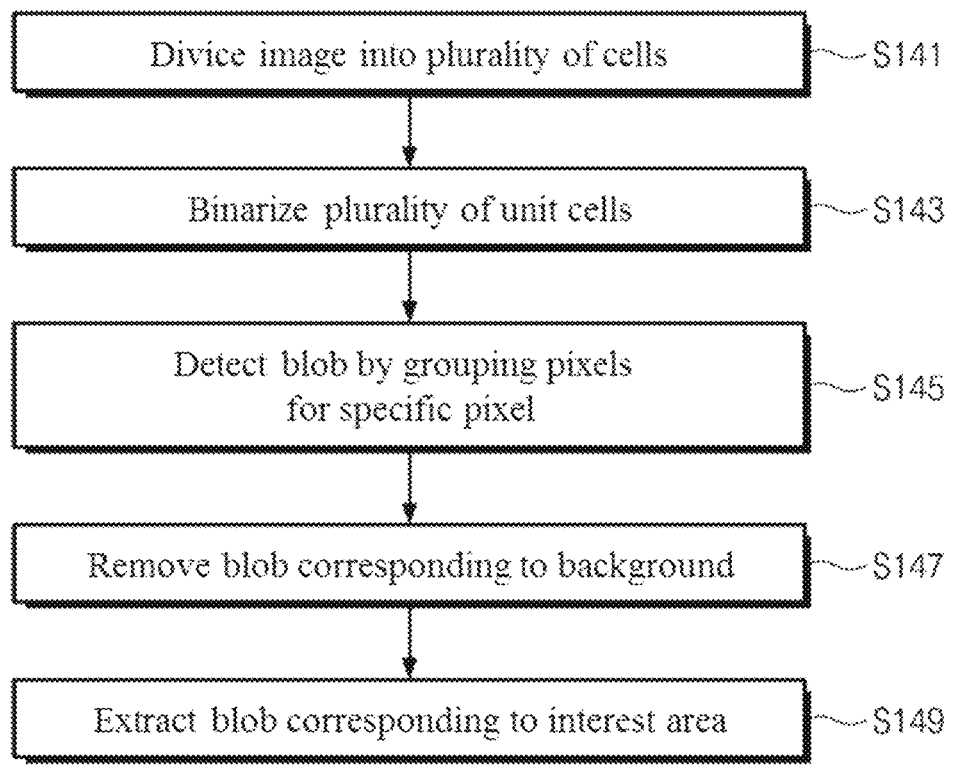

[Fig. 8A]
S143
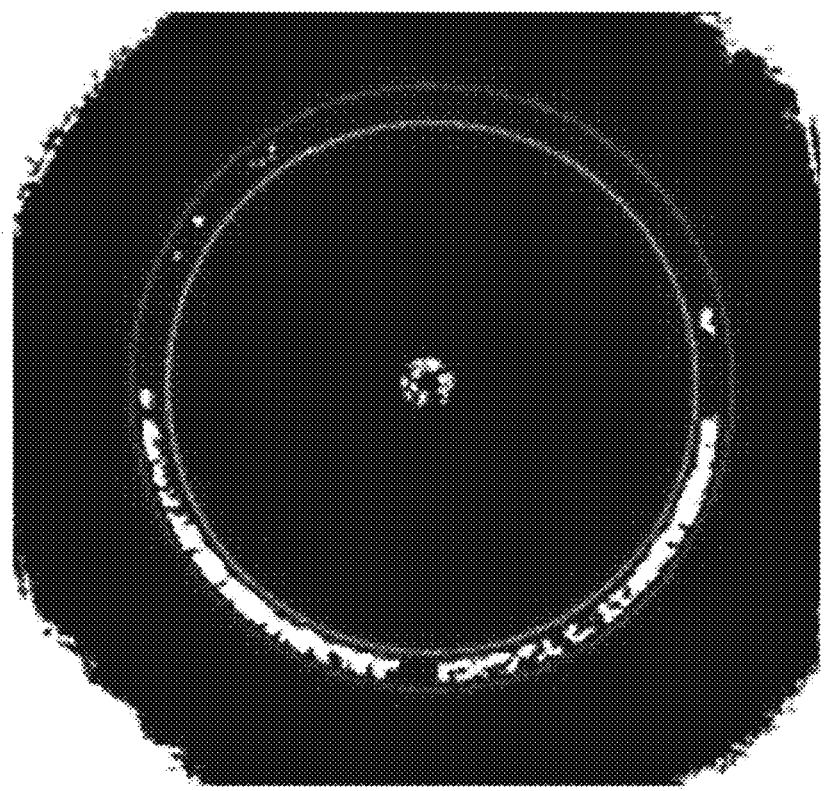

[Fig. 8B]
S143
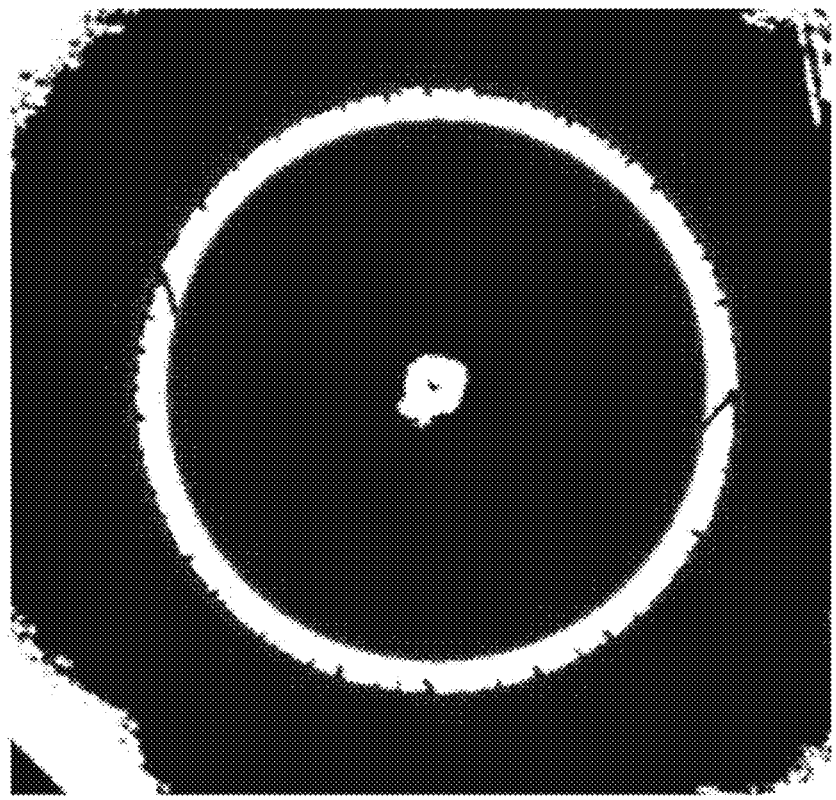

[Fig. 9A]
S147
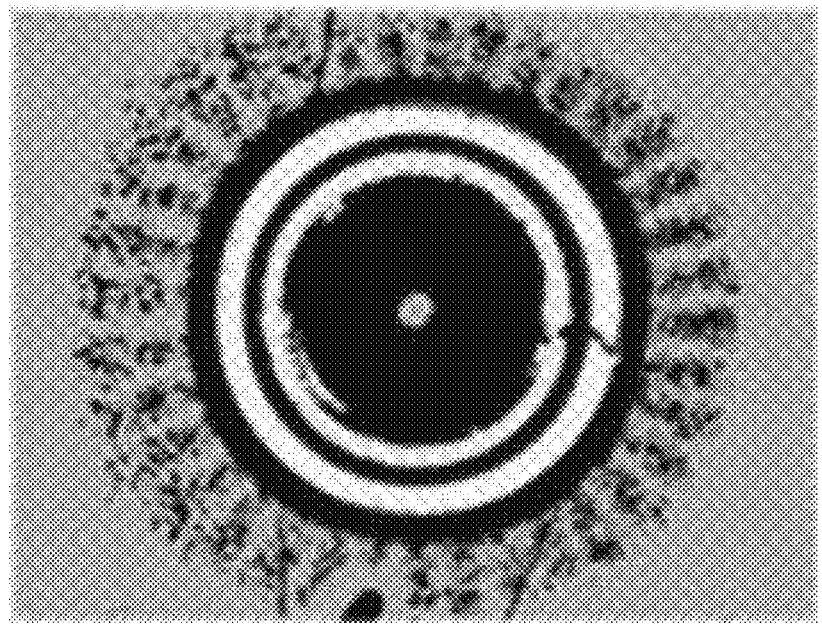

[Fig. 9B]
S147
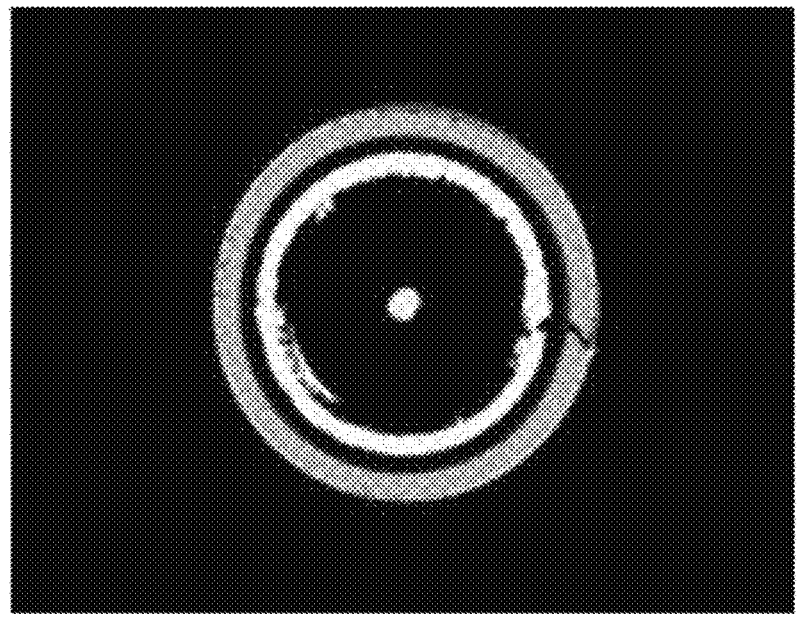

[Fig. 10A]
S149
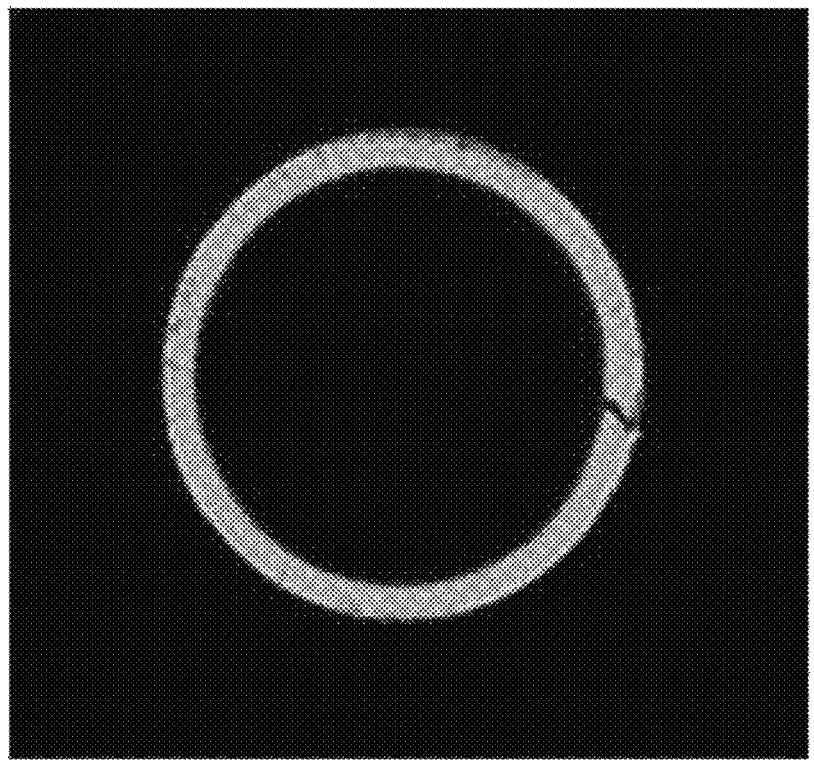

[Fig. 10B]
S149
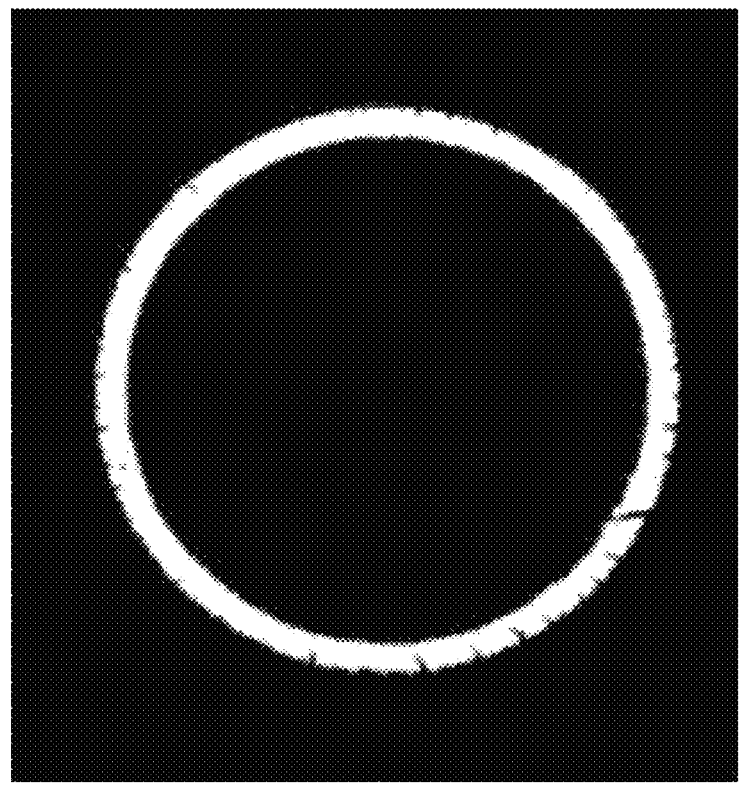

[Fig. 11]
S150
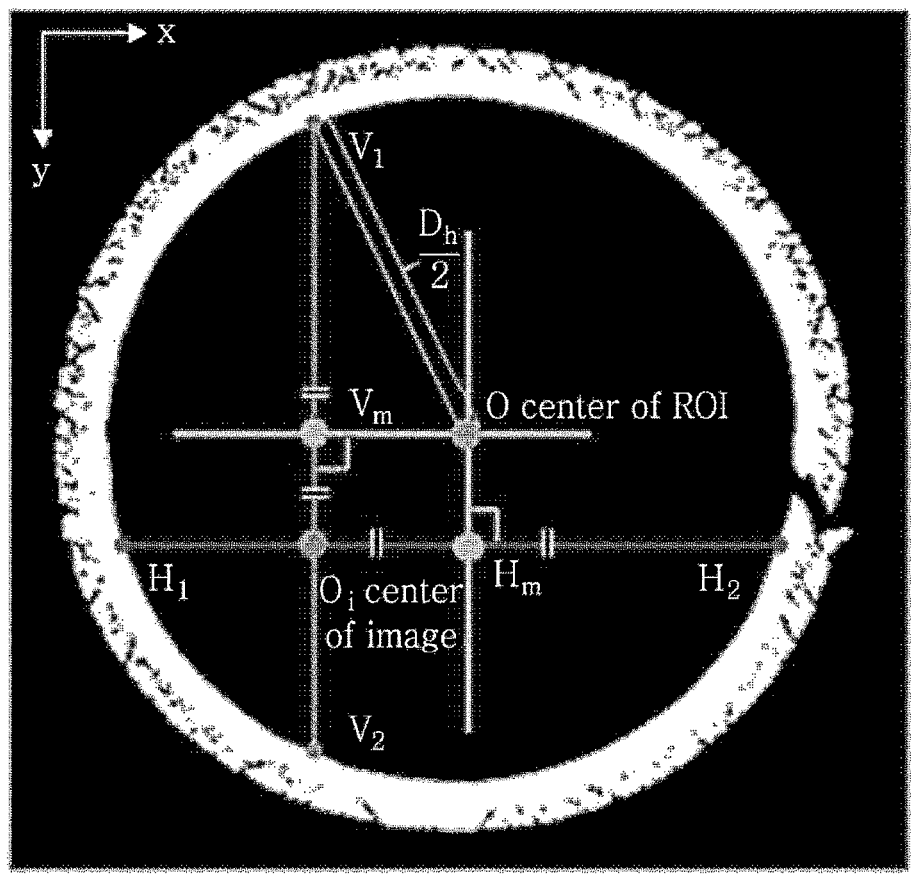

[Fig. 12A]
S160
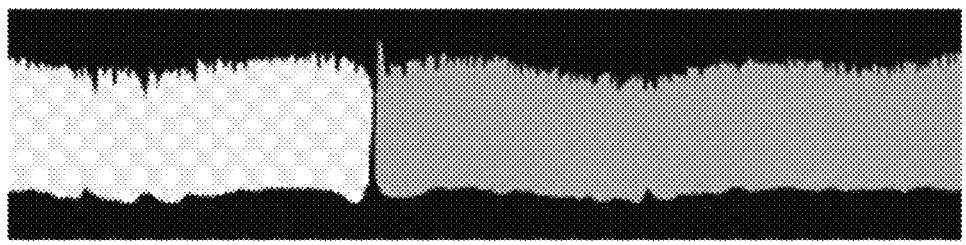

[Fig. 12B]
S160
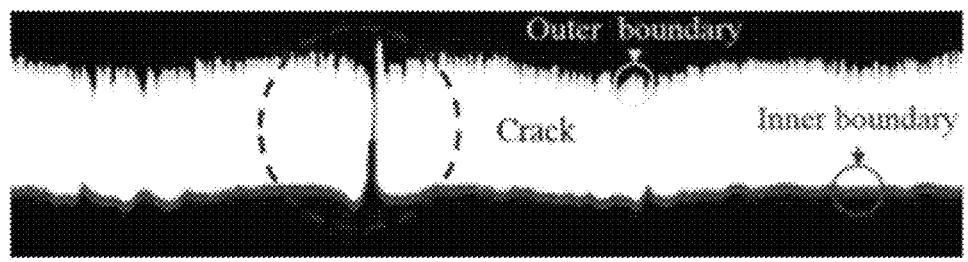

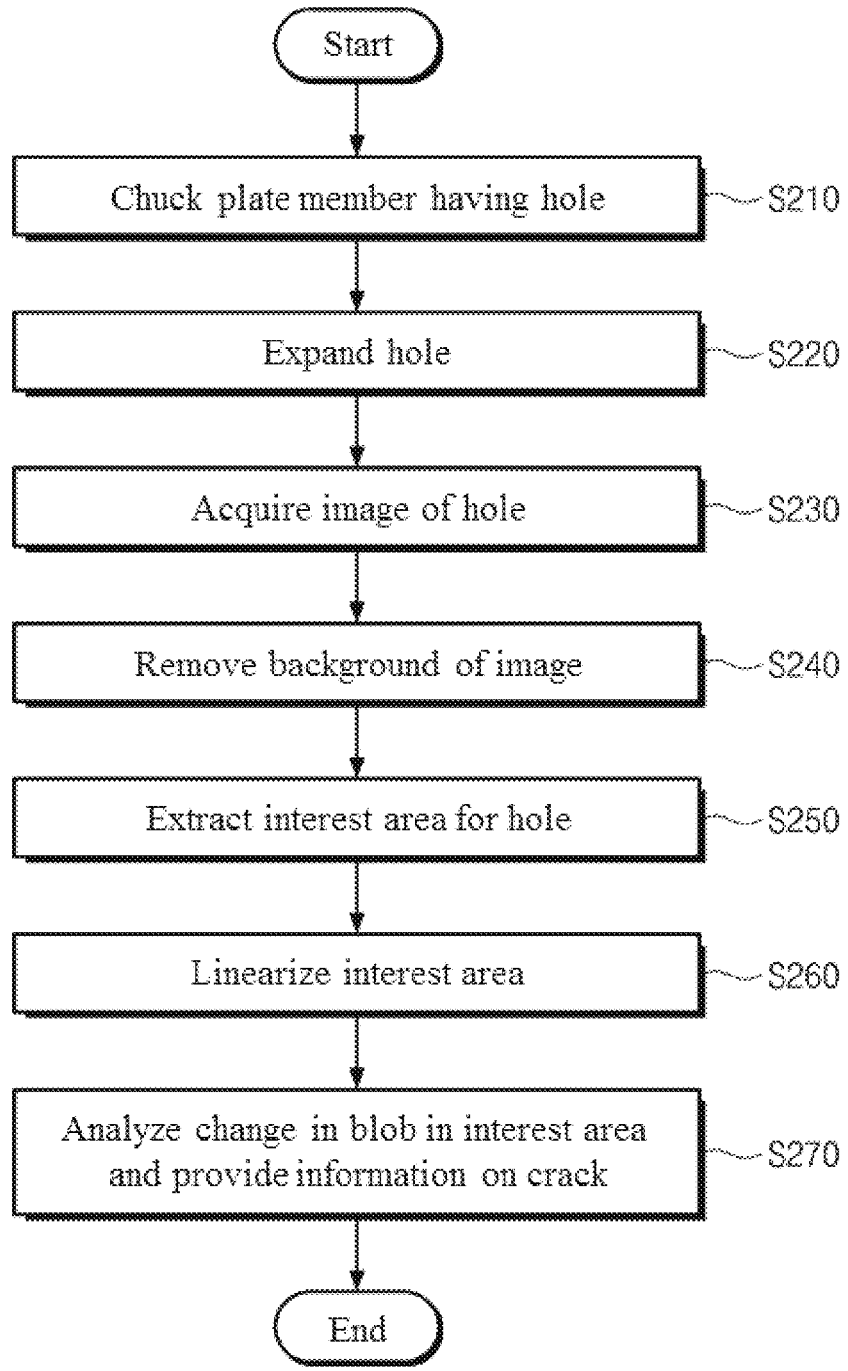
[Fig. 13]

[Fig. 14A]
S240
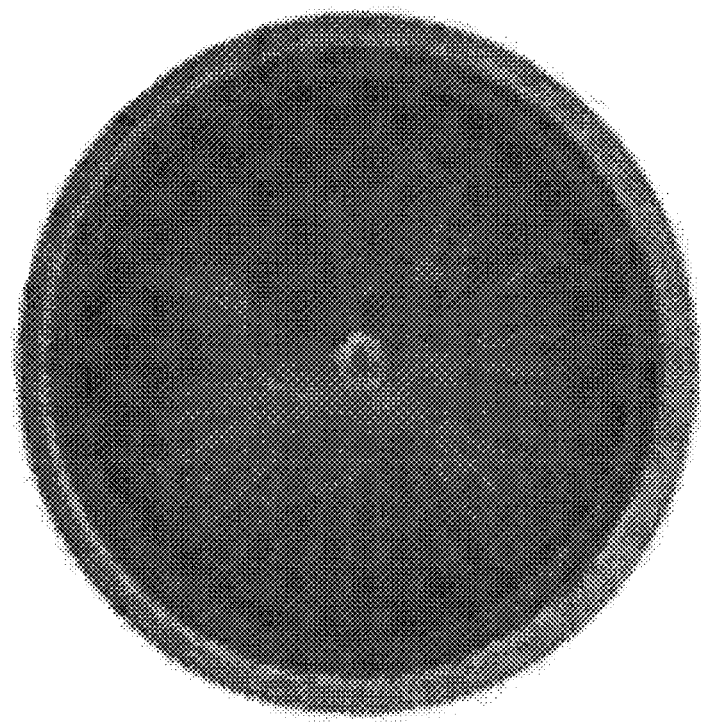

[Fig. 14B]
S240
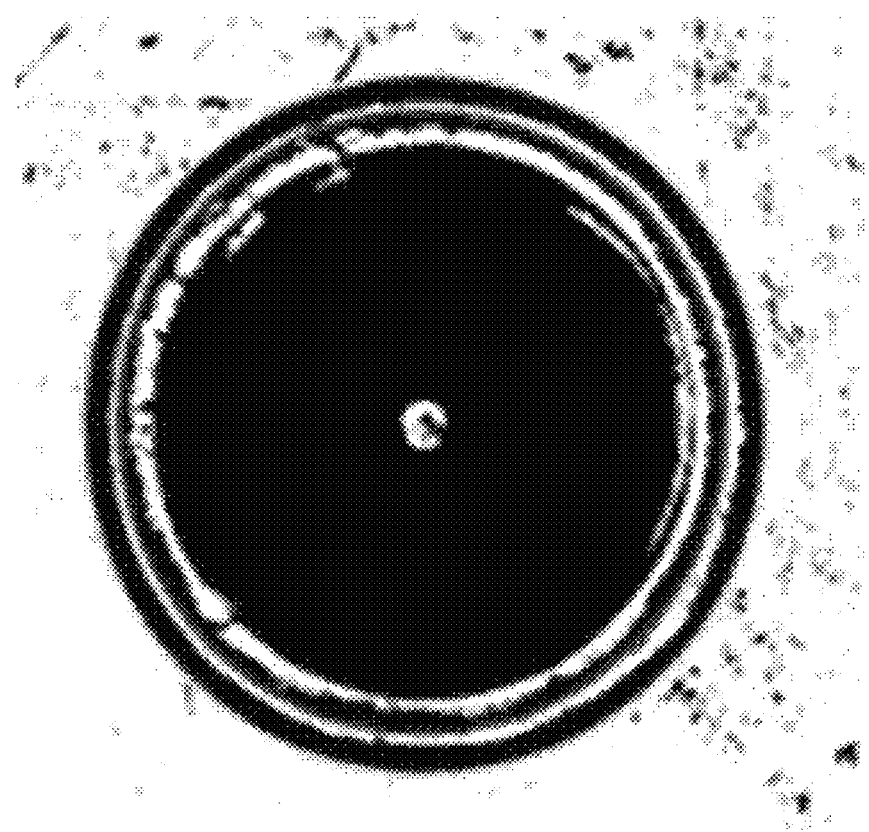

[Fig. 14C]
S240
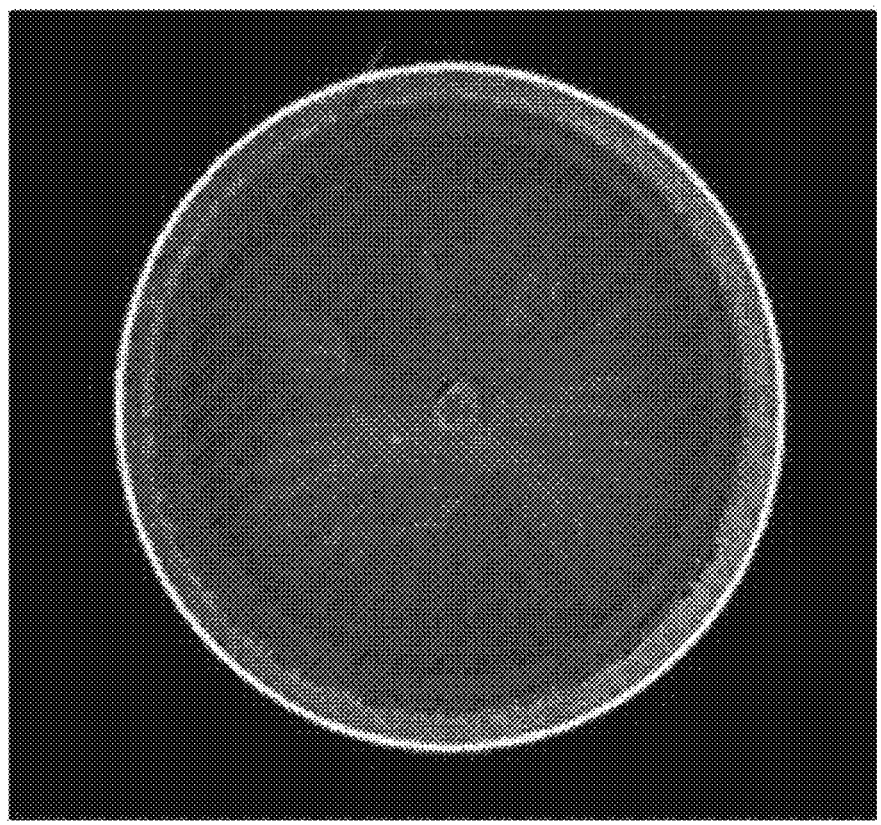

[Fig. 15]
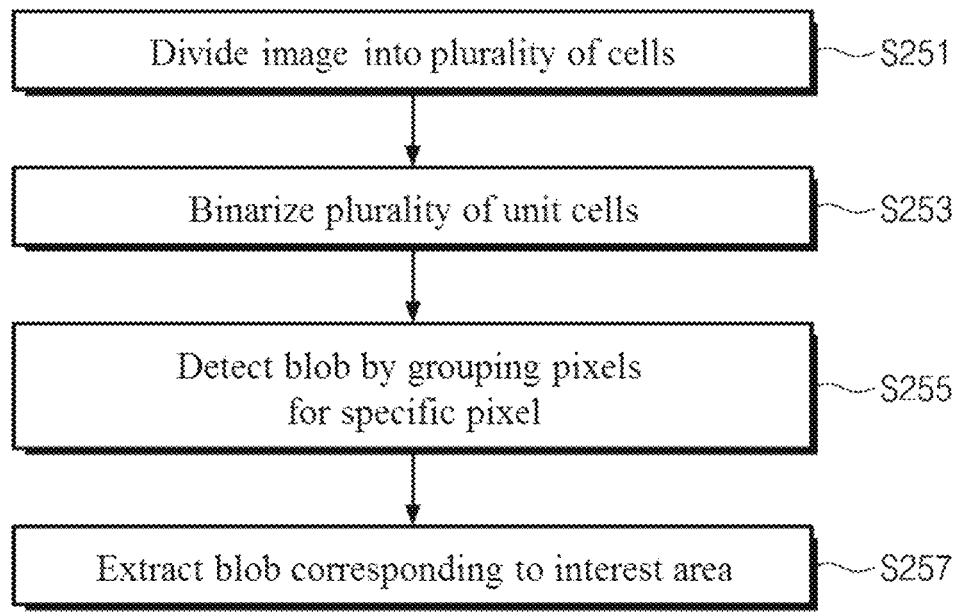

[Fig. 16A]
S253
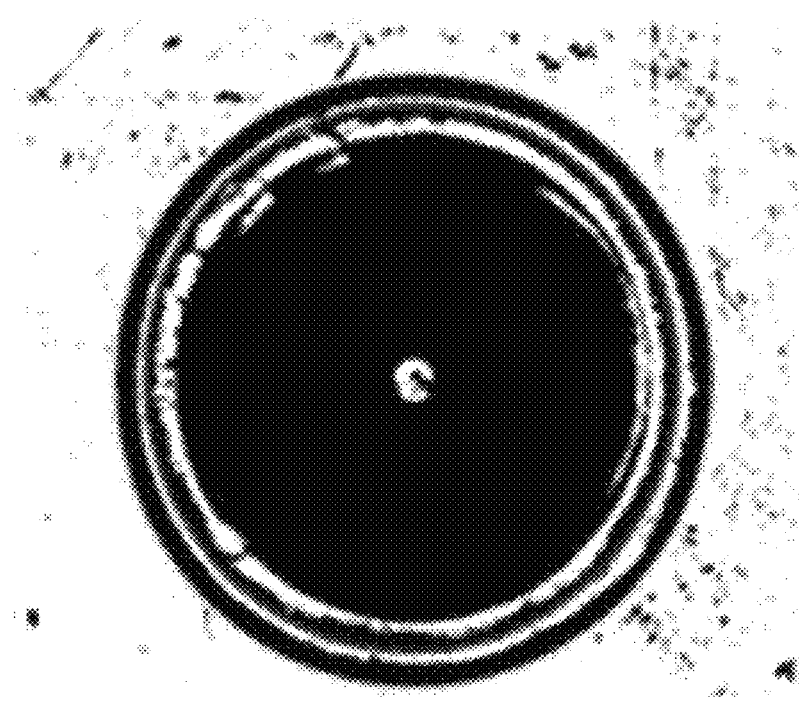

[Fig. 16B]
S253
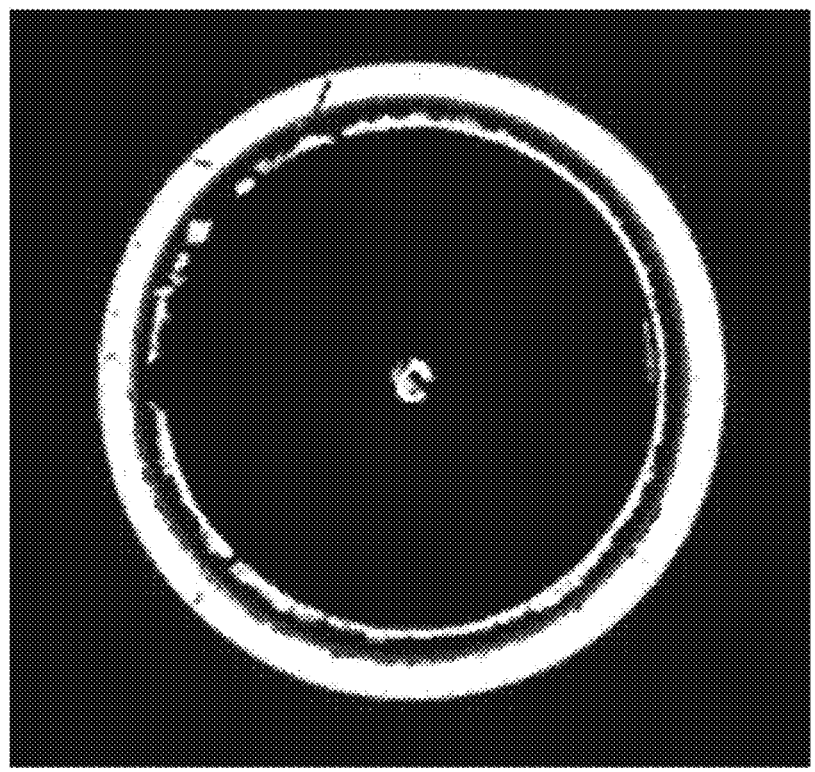

[Fig. 17A]
S257
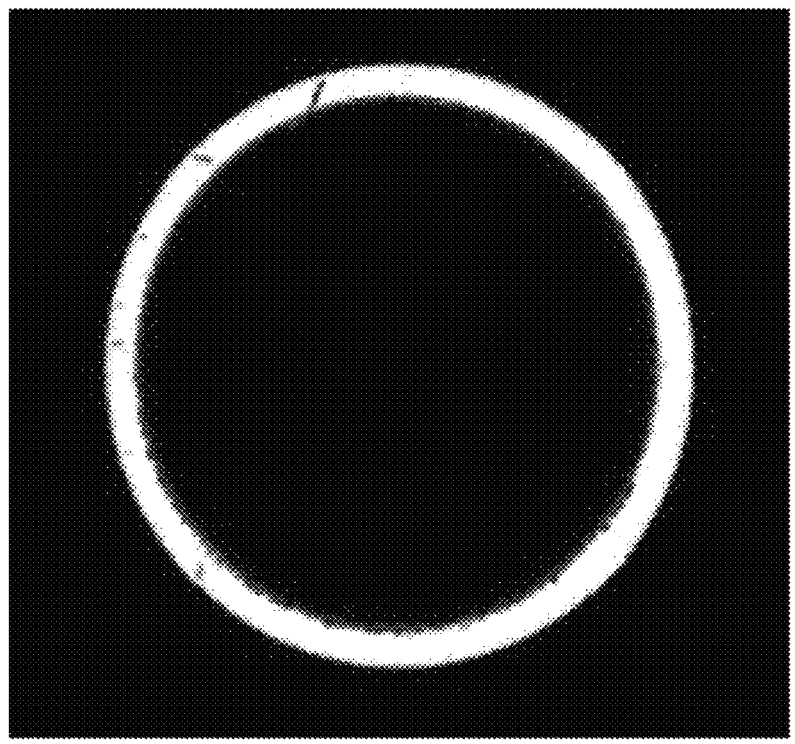

[Fig. 17B]
S257
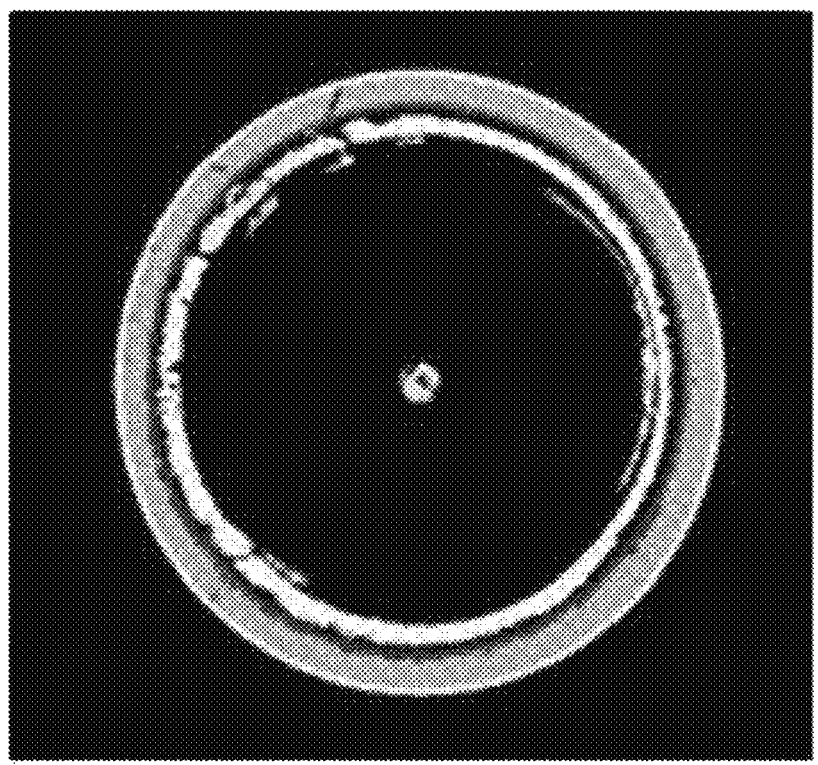

HOLE EXPANSION RATIO TESTING DEVICE, HOLE EXPANSION RATIO TESTING METHOD, AND OPERATING PROGRAM

BACKGROUND OF THE INVENTION

1. Field of the Invention

The present disclosure relates to a hole expansion ratio testing device, a hole expansion ratio testing method, and an operation program, and more particularly, to a hole expansion ratio testing device for extracting an interest area from an image of a hole, linearizing the interest area, and analyzing information of a crack, a hole expansion ratio testing method, and an operating program.

2. Description of the Prior Art

In general, a hole expansion ratio (HER) test is one of testing methods for, when a hole of a plate member having the hole is expanded, determining how the hole may be expanded without causing an error such as a crack or necking. The HER test is one of important testing methods for deriving the formability and the crack resistance of a material.

In recent years, mainly in the automobile businesses, steels of an ultra-high strength that requires a tensile strength of 10.0 GPa or more have been increasingly used. The ultra-high strength steels have an excellent tensile strength and an excellent stiffness, but the formability thereof is very low and the resistance against a crack and necking is vulnerable. Accordingly, nowadays, the formability and crack stability as well as the strength of the steel have been important consideration items in selecting steel.

For the reason, studies on method for evaluating an HER for improving precision and efficiency have been made. Because occurrence of a crack and the size of the crack are determined by observing an initial crack by the naked eyes of an operator according to the existing HER evaluation, the naked eyes and a subjective determination of the operation is involved in determining physical properties, and thus there are always problems of the reliability and the reproduction performance of the experimental results. In order to solve the problems, an evaluation method for determining occurrence of a crack by recognizing a change in a load applied by a punch has been developed, but the change in the load cannot be recognized properly when the crack is fine, and a device for determining occurrence of a crack from a change of a current applied to a test specimen, but the conductive test specimen should be separately machined in the method.

SUMMARY OF THE INVENTION

The present disclosure provides a hole expansion ratio testing device that extracts an interest area from an image of a hole, linearizes the interest area, and analyzes information of a crack, a hole expansion ratio testing method, and an operating program.

The present disclosure also provides a hole expansion ratio testing device that determines whether a plate member having a hole has been plated by itself, and change an analysis method by itself according to the plating state, a hole expansion ratio testing method, and an operating program The technical objectives of the present disclosure are not limited to the above-described ones.

In order to solve the technical problems, the present disclosure provides a hole expansion ratio testing device, a hole expansion ratio testing method, and an operation program.

In accordance with an aspect of the present disclosure, there is provided a hole expansion ratio testing device including: a chucking unit configured to chuck a plate member having a hole; a punching unit inserted into the hole and configured to expand the hole; an image acquisition unit configured to acquire an image of the hole expanded by the punching unit; and an analysis unit configured to extract an interest area corresponding to the hole from the acquired image, linearize the interest area, and provide information on a crack as a blob changes due to the linearization.

According to an embodiment, the analysis unit may extract the interest area by dividing the image of the acquired hole into a plurality of unit cells, and binarize the plurality of unit cells by applying independent threshold values for the unit cells.

According to an embodiment, the analysis unit may select a specific pixel from the binarized image, detect blobs by grouping adjacent pixels having the same gray scale as the specific pixel, remove the largest blob from the detected blobs, and provide, among the blobs left after the removal, a blob that is most distant from the center of the image as the interest area.

According to an embodiment, the analysis unit may vary a sequence, in which backgrounds are removed from the acquired image, according to whether the plate member is plated.

According to an embodiment, when the plate member is plated, the analysis unit may remove a background defined as an area reflected due to the plating, and extract the interest area from the image, from which the background has been removed.

According to an embodiment, the analysis unit may select a specific pixel from the binarized image, detect blobs by grouping adjacent pixels having the same gray scale as the specific pixel, remove the largest blob from the detected blobs, and provide a blob that is most distant from the center of the image as the interest area.

According to an embodiment, the hole expansion ratio testing device may further include a control unit configured to control the punching unit, and when it is determined through the analysis unit that there is a crack in the plate member, the control unit may control the punching unit to stop the movement of the punching unit, and the analysis unit may derive a size and a hole expansion ratio of the hole in a state in which the punching unit is stopped.

According to an embodiment, the analysis unit may linearize the extracted interest area with reference to an arbitrary point.

According to an embodiment, the analysis unit may provide information on the crack according to the numbers of the blobs before and after the linearization of the interest area.

According to an embodiment, the analysis unit may provide information on the crack according to whether an outer boundary and an inner boundary of the blob in the interest area meet each other after the linearization.

In accordance with an aspect of the present disclosure, there is provided a hole expansion ratio testing method including: chucking a plate member having a hole; expanding the hole by inserting the punching unit into the interior of the hole; acquiring an image of the hole while the hole is expanded; extracting an interest area corresponding to the hole from the acquired image; linearizing the interest area; and providing information on a crack as a blob changes due to the linearization.

According to an embodiment, the hole expansion ratio testing method may include determining whether the plate member has been plated, and the extracting of the interest area includes: when it is determined that the plate member has not been plated, removing a background of the image, and the hole expansion ratio testing method may further include, when it is determined that the plate member has been plated, removing the background of the image, before the extracting of the interest area.

According to an embodiment, the providing of the information on the crack may include considering at least one of information on the numbers of the blobs before and after the linearization of the interest area and information on whether an outer boundary and an inner boundary of the blob in the interest area meet each other after the linearization According to an embodiment, the extracting of the interest area may include: when the plate member has not been plated, selecting a specific pixel from the binarized image, and detecting blobs by grouping adjacent pixels having the same gray scale as the specific pixel; and removing the largest blob from the detected blobs, and providing, among the blobs left after the removal, a blob that is most distant from the center of the image as the interest area, and when the plate member has been plated, selecting a specific pixel from the binarized image, and detecting blobs by grouping adjacent pixels having the same gray scale as the specific pixel; and providing a blob that is most distance from the center of the image as the interest area.

In accordance with another aspect of the present disclosure, there is provided a hole expansion ratio testing program stored in a medium to execute operations of: chucking a plate member having a hole; expanding the hole by inserting the punching unit into the interior of the hole; acquiring an image of the hole while the hole is expanded; extracting an interest area corresponding to the hole from the acquired image; linearizing the interest area; and providing information on a crack as a blob changes due to the linearization.

According to the embodiment of the present disclosure, the hole expansion ratio testing device may include a chucking unit configured to chuck a plate member having a hole, a punching unit inserted into the hole and configured to expand the hole, an image acquisition unit configured to acquire an image of the hole expanded by the punching unit, and an analysis unit configured to extract an interest area corresponding to the hole from the acquired image, linearize the interest area, and provide information on a crack as a blob changes due to the linearization.

Through this, the hole expansion ratio testing device may automate the HER process, and may provide crack information while excluding the naked eyes and the determination of a user. Through this, the reliability of a result of the hole extension ratio test may be enhanced, and a HER analysis system having a high reproduction performance may be provided.

In addition, the present disclosure may further include an operation of determining whether the plate member has been plated, by the hole expansion ratio testing device itself, and an operation of extracting the interest area may be changed according to the plate member has been coated. Through this, a result of a high reliability may be provided without being limited by whether the plate member is coated, and HER results for various kinds of steel plates may be secured.

BRIEF DESCRIPTION OF THE DRAWINGS

The above and other objects, features, and advantages of the present invention will be more apparent from the following detailed description taken in conjunction with the accompanying drawings, in which:

FIG. 1 is a cross-sectional view illustrating a hole expansion ratio testing device according to an embodiment of the present disclosure;

FIG. 2 is a flowchart illustrating a hole expansion ratio testing method for a non-plated plate member according to an embodiment of the present disclosure;

FIG. 3 is a cross-sectional view illustrating operation S110 according to an embodiment of the present disclosure;

FIGS. 4A and 4B are cross-sectional views illustrating operation S120 according to an embodiment of the present disclosure;

FIG. 5 is a picture illustrating operation S130 according to an embodiment of the present disclosure;

FIG. 6 is a flowchart illustrating operation S140 according to an embodiment of the present disclosure;

Figure 7:
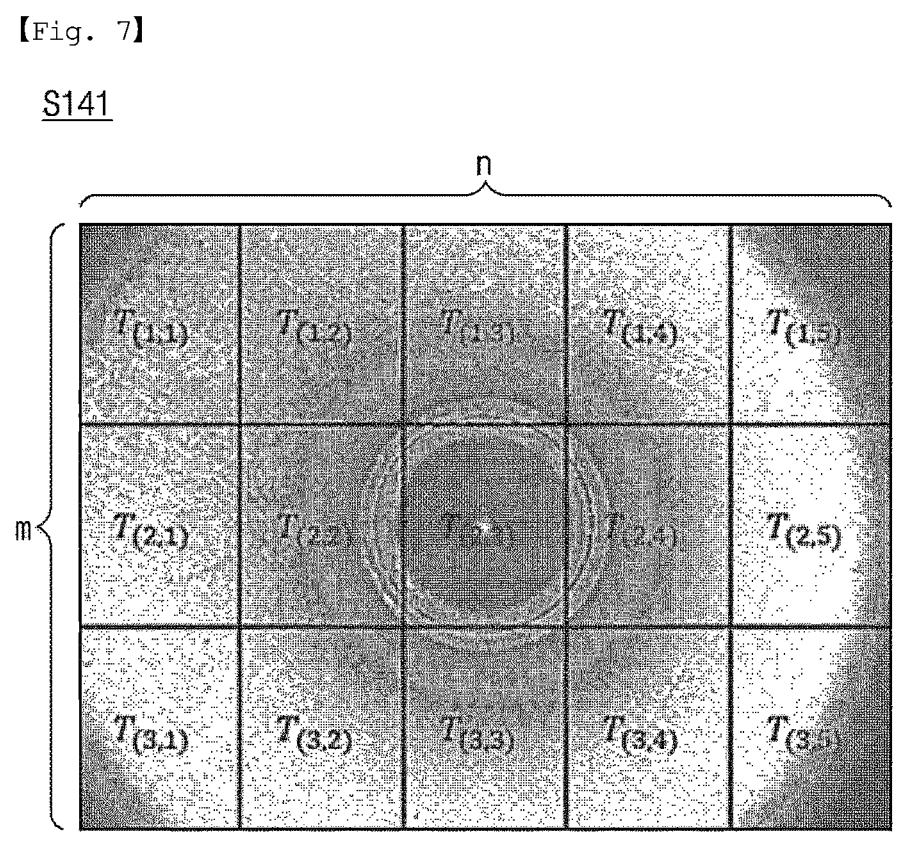

FIG. 7 is a picture illustrating operation S141 according to an embodiment of the present disclosure;

FIGS. 8A and 8B are pictures illustrating operation S143 according to an embodiment of the present disclosure;

FIGS. 9A and 9B are pictures illustrating operation S147 according to an embodiment of the present disclosure;

FIGS. 10A and 10B are pictures illustrating operation S149 according to an embodiment of the present disclosure;

FIG. 11 is a picture illustrating operation S150 according to an embodiment of the present disclosure;

FIGS. 12A and 12B are pictures illustrating operation S160 according to an embodiment of the present disclosure;

FIG. 13 is a flowchart illustrating a hole expansion ratio testing method for a plated plate member according to an embodiment of the present disclosure;

FIGS. 14A, 14B, and 14C are pictures illustrating operation S240 according to an embodiment of the present disclosure;

FIG. 15 is a flowchart illustrating operation S250 according to an embodiment of the present disclosure;

FIGS. 16A and 16B are pictures illustrating operation S253 according to an embodiment of the present disclosure; and FIGS. 17A and 17B are pictures illustrating operation S257 according to an embodiment of the present disclosure.

DETAILED DESCRIPTION OF THE EXEMPLARY EMBODIMENTS

Hereinafter, preferred embodiments of the present disclosure will be described in detail with reference to the accompanying drawings. However, the technical spirit of the present disclosure is not limited to the embodiments, but may be realized in different forms. The embodiments introduced here are provided to sufficiently deliver the spirit of the present disclosure to those skilled in the art so that the disclosed contents may become thorough and complete.

When it is mentioned in the specification that one element is on another element, it means that the first element may be directly formed on the second element or a third element may be interposed between the first element and the second element. Further, in the drawings, shapes and the thicknesses of areas are exaggerated for efficient description of the technical contents.

Further, in the various embodiments of the present disclosure, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments illustrated here include their complementary embodiments. Further, the term "and/or" in the specification is used to include at least one of the elements enumerated in the specification.

In the specification, the terms of a singular form may include plural forms unless otherwise specified. In the specification, the terms "including" and "having" are used to designate that the features, the numbers, the steps, the elements, or combinations thereof described in the specification are present, and may be understood that one or more other features, numbers, step, elements, or combinations thereof may be added. Further, in the specification, "connected to" is used to mean a plurality of elements are indirectly or directly connected to each other.

Further, the terms, such as "unit", "-er, -or", and "module" described in the specification mean a unit for processing at least one function or operation, and may be implemented by hardware, software, or a combination of hardware and software.

Further, in the following description of the present disclosure, a detailed description of known functions and configurations incorporated herein will be omitted when it may make the subject matter of the present disclosure rather unclear.

According to an aspect of the present disclosure, a hole expansion ratio testing device that automatically perform and analyze a hole expansion ratio test (HER) may be provided. For example, the hole expansion ratio testing device may include a chucking unit and a punching unit to expand a hole of a plate member having the hole, and may include an image acquisition unit and an analysis unit to acquire an image of the hole, analyze the acquired image, and provide information on a hole expansion ratio and a crack. Through this, the hole expansion ratio testing device may automate the HER process, and may improve productivity and quality. Furthermore, a standardized hole expansion ratio testing method may be provided.

According to another aspect of the present disclosure, a hole expansion ratio testing method for quantitatively providing information on a crack in a plate member may be provided. For example, the analysis unit may extract an interest area from an image of a hole secured by the image acquisition unit, analyze the interest area through a linearization process, and provide information on a crack, in which the naked eyes and determination of a user are excluded. Through this, the reliability of a result of the hole extension ratio test may be enhanced, and a HER analysis system having a high reproduction performance may be provided.

According to another aspect of the present disclosure, a hole expansion ratio testing method for considering parameters according to a state of a surface of a plate member may be provided. For example, the hole expansion ratio testing device may further include an operation of determining whether the plate member is plated, by itself, and may change an operation of extracting an interest area according to the plate member is coated. Through this, a result of a high reliability may be provided without being limited by whether the plate member is coated, and HER results for various grades of steel plates may be secured.

FIG. 1 is a cross-sectional view illustrating a hole expansion ratio testing device according to an embodiment of the present disclosure.

Referring to FIG. 1, the hole expansion ratio testing device 100 according to the embodiment of the present disclosure may include one or more of a chucking unit 110, a punching unit 120, an image acquisition unit 130, a control unit 140, and an analysis unit 150.

The chucking unit 110 may chuck a plate member P, in which a hole H is punched for a hole expansion test. For example, the chucking unit 110 may include a first die 111 and a second die 115, and the plate member P may be fixed and chucked between the first die 111 and the second die 115. The first die 111 may have a plate shape, and may have a first opening 113 that passes through the first die 111. The second die 115 may have a plate shape, and may have a second opening 117 that passes through the second die 115. According to the embodiment, the second opening 117 may be formed on a straight line that passes through the center of the first opening 113. Then, a line that commonly passes through the first opening 113 and the second opening 117 may be defined as a center line L. According to the embodiment, the diameter of the first opening 113 may be larger than or equal to the diameter of the second opening 117.

The punching unit 120 may be inserted into the hole H to expand the hole H. The punching unit 120 may be located on the center line L. According to the embodiment, the punching unit 120 may move in a vertical direction M along the center line L by the control unit 140, which will be described below. For example, the punching unit 120 may be lifted in the vertical direction to expand the size of the hole H punched in the plate member P. In contrast, the punching unit 120 may be lowered in the vertical direction to be inserted into the second opening 117. According to the embodiment, an upper end of the punching unit 120 may have any one of a conical shape having a predetermined angle, a cylindrical shape of a planar shape, and a spherical shape. Although it has been described in the embodiment that the upper end of the punching unit 120 has a conical shape, the present disclosure is not limited thereto.

The image acquisition unit 130 is equipment having a predetermined photographing area I, and may acquire an image of the hole H. According to the embodiment, the image acquisition unit 130 may be located at one point of the center line L, which is spaced apart toward the upper end of the plate member P by a predetermined distance. The image acquisition unit 130 may photograph the hole H in real time, and may transmit the captured image to the analysis unit 150, which will be described below. The image acquisition unit 130 may include a camera, and may include a charge-coupled device (CCD) camera.

The control unit 140 may be electrically connected to the chucking unit 110, the punching unit 120, and the image acquisition unit 130, and may control one or more of the chucking unit 110, the punching unit 120, and the image acquisition unit 130. For example, the control unit 140 may lower or lift any one or more of the first die 111 and the second die 115 in the direction of the center line L to control the plate member P to be chucked. Furthermore, the control unit 140 may lower or lift the punching unit 120 in the direction of the center line L to expand the punched hole H of the plate member P. Furthermore, the control unit 140 may control a photographing condition of the image acquisition unit 130, and may control the image captured by the image acquisition unit 130 to be transmitted to the analysis unit 150, which will be described below.

The analysis unit 150 may be electrically connected to the image acquisition unit 130 and the control unit 140, and may analyze the image provided from the image acquisition unit 130 and provide information of a crack. In detail, the analysis unit 150 may extract an interest area corresponding to the hole H from the image acquired by the image acquisition unit 130, and may linearize the interest area. Then, the analysis unit 150 may provide the information on a crack as a blob changes due to the linearization.

Until now, the hole expansion ratio testing device 100 according to the embodiment of the present disclosure has been described. Hereinafter, a hole expansion ratio testing method for a non-plated plate member will be described through FIGS. 2 to 17B.

According to the embodiment of the present disclosure, the hole expansion ratio testing method may include any one or more of an operation of chucking a plate member having a hole, an operation of expanding the hole by inserting the punching unit into the interior of the hole, an operation of acquiring an image of the hole while the hole is expanded, an operation of extracting an interest area corresponding to the hole from the acquired image, an operation of linearizing the interest area, and an operation of providing information on a crack as a blob changes due to the linearization.

According to the embodiment, the hole expansion ratio testing device may further include an operation of determining whether the plate member has been plated. The operation of determining whether the plate member has been plated may include any one or more of a method of inputting whether the plate member has been plated, by a user, and a method of determining whether the plate has been plated by analyzing the image of the hole by the hole expansion ratio testing device by itself.

For example, the control unit may determine that the plate member is a non-plated member when the reflection degree of a background area (for example, the outside of the interest area) is a predetermined reference hereinafter, and unlike this, may determine that the plate member is a plated member when the reflection degree of the background area (for example, the outside of the interest area) is more than the predetermined reference.

When it is determined that the plate member has not been plated, the hole expansion ratio testing device may provide the information of a crack according to the flowchart disclosed in FIG. 2. Furthermore, when it is determined that the plate member has been plated, the hole expansion ratio testing device may provide the information on a crack according to the flowchart disclosed in FIG. 13. In the specification, the hole expansion ratio testing method for a non-plated plate member disclosed in FIG. 2 will be described, and the hole expansion ratio testing method for a plated plate member will be described later through FIG. 13.

FIG. 2 is a flowchart illustrating a hole expansion ratio testing method for a non-plated plate member according to an embodiment of the present disclosure. FIG. 3 is a cross-sectional view illustrating operation S110 according to an embodiment of the present disclosure. FIGS. 4A and 4B are cross-sectional views illustrating operation S120 according to an embodiment of the present disclosure. FIG. 5 is a picture illustrating operation S130 according to an embodiment of the present disclosure. FIG. 6 is a flowchart illustrating operation S140 according to an embodiment of the present disclosure. FIG. 7 is a picture illustrating operation S141 according to an embodiment of the present disclosure. FIGS. 8A and 8B are pictures illustrating operation S143 according to an embodiment of the present disclosure. FIGS. 9A and 9B are pictures illustrating operation S147 according to an embodiment of the present disclosure. FIGS. 10A and 10B are pictures illustrating operation S149 according to an embodiment of the present disclosure. FIG. 11 is a picture illustrating operation S150 according to an embodiment of the present disclosure. FIGS. 12A and 12B are pictures illustrating operation S160 according to an embodiment of the present disclosure.

Referring to FIG. 2, the hole expansion ratio testing method for a non-plated plate member may include any one or more of an operation S110 of chucking a plate member having a hole, an operation S120 of expanding the hole, an operation S130 of acquiring an image of the hole, an operation S140 of extracting an interest area for the hole, an operation S150 of linearizing the interest area, and an operation S160 of analyzing a change in a blob in the interest area and providing information on a crack.

Operation S110 The operation S110 of chucking the plate member having the hole is an operation of placing the plate member P between |the first jig 111 and a second jig 115|[V1] and chucking the plate member by pressing the plate member. In detail, referring to FIG. 3, the plate member P may be positioned on one surface between the first jig 111 and the second jig 115. Then, the hole H formed in the plate member P may be located on a straight line that passes through the centers of the first opening 113 of the first jig 111 and the second opening 117 of the second jig 115. In other words, the hole H may be located in a row on the center line L that commonly passes the first opening 113 and the second opening 117, and may be arranged side by side in the sequence of the first opening 113, the hole H, and the second opening 117.

Although it is illustrated that the first jig 111 is pressed in the direction D, in which the second jig 115 is located, it is apparent to an ordinary person in the art that the second jig 115 may be pressed in a direction, in which the first jig 115 is located, or in a direction D, in which the first jig 111 and the second jig 115 face each other.

Operation S120

Referring back to FIG. 2, the operation S120 of expanding the hole is an operation of expanding the hole H formed in the plate member P, by the punching unit 120 inserted into the second opening 117.

In detail, referring to FIG. 4A, the punching unit 120 may be inserted into the second opening 117 formed in the second jig 115. Then, the image acquisition unit 130, the hole H, and the punching unit 120 may be arranged side by side on the center line. According to the embodiment, the control unit 140 may control the punching unit 120 to move in a direction U, in which the punching unit 120 is vertically lifted along the center line L.

Referring to FIG. 4B, the punching unit 120 may expand the hole H by pressing a lower portion of the hole H formed in the plate member P.

Operation S130

Referring back to FIG. 2, the operation S130 of acquiring an image of a hole is an operation of acquiring an image of the hole H by the analysis unit 150 through the image acquisition unit 130.

For example, the analysis unit 150 may acquire the image of the hole H in real time through the image acquisition unit 130 when the hole H is expanded.

Referring to FIG. 5, the analysis unit 150 may receive the image of the hole H formed on one surface of the plate member P, from the image acquisition unit 130. The image may provide information on an outer peripheral surface (a blue-colored circle) and an inner peripheral surface (a red-colored circle) of the hole H. Then, the area between the outer peripheral surface (the blue-colored circle) and the inner peripheral surface (the red-colored circle) of the hole H may be defined as an interest area. According to the embodiment, the analysis unit 150 may further include a function of converting the image into a gray scale when the image does not appear in a gray scale.

Operation S140

The operation S140 of extracting the interest area of the hole is an operation of extracting the interest area by converting the image. Referring to FIG. 6, the operation S140 of extracting the interest area of the hole may further include any one or more of an operation S141 of dividing the image into a plurality of cells, an operation S143 of binarizing the plurality of unit cells, an operation S145 of detecting a blob by grouping the unit cells for a specific pixel, an operation S147 of removing a blob corresponding to a background, and an operation S149 of extracting a blob corresponding to the interest area.

Operation S141

The operation S141 of dividing the image into a plurality of cells is an operation of dividing the image into unit cells by the analysis unit 150. Referring to FIG. 7, the analysis unit 150 may divide the image received from the image acquisition unit 130 into unit cells of m by n. Through this, the analysis unit 150 may set corresponding sections for the respective unit cells.

Operation S143

Referring back to FIG. 6, the operation S143 of binarizing the plurality of unit cells is an operation of binarizing the image divided into the plurality of unit cells. The binarization is a process of dividing the image into pixels and classifying pixels having a gray scale of a specific threshold value or more, with reference to a gray scale value for each of the pixels, as a white color and pixels having a gray scale of the specific threshold value or less as a black color. Then, the binarizations may be classified into a global binarization and an adaptive binarization according to methods of applying the threshold value. In the global binarization, one threshold value may be applied to the entire image area. Meanwhile, in the adaptive binarization, independent threshold values may be applied to the respective unit cells. According to the embodiment of the present disclosure, the analysis unit 150 may adaptive-binarizes the image to classify the interest area on the image.

Unlike the embodiment of the present disclosure, if the image is global-binarized, as disclosed in FIG. 8A, it can be identified that only a partial area of the areas is distinguished while the section between the outer peripheral surface (a blue-colored circle) and the inner peripheral surface (a red-colored circle) of the hole H is not clearly distinguished.

However, if the image is adaptive-binarized according to the embodiment of the present disclosure, as illustrated in FIG. 8B, the section between the outer peripheral surface (a blue-colored circle) and the inner peripheral surface (a red-colored circle) of the hole H may be clearly distinguished. Through this, the analysis unit 150 may distinguish the interest area between the outer peripheral surface (a blue-colored circle) and the inner peripheral surface (a red-colored circle) of the hole H.

Operation S145

Referring back to FIG. 6, the operation S145 of detecting a blob by grouping the pixels is a process of detecting a blob in the binarized image, by the analysis unit 150. The blob detection means that a specific pixel is selected and adjacent pixels having the same gray scale as that of the specific pixel are grouped. For example, the analysis unit 150 may select, in the binarized image, pixels classified as a white color, that is, pixels having a gray scale of 255, as target pixels. The analysis unit 150 may group adjacent pixels having the same gray scale when the pixels located on the upper/lower and left/right diagonal lines with respect to the target pixel have the same gray scale as the target pixel. The grouped pixels may be defined as one blob. Through the process, the binarized image may have a plurality of blobs.

Operation S147

The operation S147 of removing a blob corresponding to the background is an operation of removing, among the detected blobs, a blob corresponding to the background. For example, referring to FIG. 9A, the image may have a plurality of blobs. Then, the analysis unit 150 may remove the blob corresponding to the background by removing the largest blob. Through this, the image of FIG. 9B, from which background noise has been removed, may be obtained.

Operation S149

Referring back to FIG. 6, the operation S149 of extracting a blob corresponding to the interest area is an operation of extracting the interest area by removing the remaining blob corresponding to the noise, from the background secured through operation S147. For example, referring to FIG. 10A, the analysis unit 150 may remove the remaining blobs, except for the blob that is most distant from the center of the image, from the image, from which the blobs corresponding to the background has been removed in operation S147. Then, the blob that is most distant from the center of the image is a blob corresponding to the interest area. Through this, the analysis unit 150 may provide a blob corresponding to the interest area as disclosed in FIG. 10B.

Operation S150

Referring back to FIG. 2, the operation S150 of linearizing the interest area is an operation of linearizing the circular interest area to analyze the blob. The analysis unit 150 may linearize the circular interest area with respect to the center point of the circular interest area. Here, a process of deriving the center point of the circuit interest area will be described.

Referring to FIG. 11, the analysis unit 150 may draw a horizontal line and a vertical line that pass through the center point with reference to the center point of the image. Then, the analysis unit 150 may define one point that contacts the interest area first when the vertical line is extended as $V_1$, and may define another point as $V_2$. Through the same process, the analysis unit 150 may define one point that contacts the interest area first when the horizontal line is extended as $H_1$, and may define another point as $H_2$. The analysis unit 150 may derive one point, the X coordinate of which is $H_m$ that is the center point of $H_1$ and $H_2$ and the Y coordinate of which is $V_m$ that is the center point of $V_1$ and $V_2$. The one point may be defined as the center of the circular interest area. Through the process, the analysis unit 150 may derive the center of the circular interest area, and may linearize the interest area with reference to the center of the circular interest area. Through this, the analysis unit 150 may analyze a crack more efficiently than when the interest area has a circular state.

Operation S160

Referring back to FIG. 2, the operation S160 of analyzing a change in a blob in the interest area and providing information of a crack is an operation of analyzing the interest area linearized through operation S150 and providing information on a crack such as the size and the number of cracks. The analysis unit 150 may derive information on a crack through any one or more of a method of analyzing the number of independent blobs and a method of extracting and analyzing an inner boundary and an outer boundary of the blob.

Referring to FIG. 12B, the analysis unit 150 may determine whether a crack occurs by recognizing the number of the independent blobs. In other words, the analysis unit 150 may acquire the blob linearized through operation S150, and when the number of the linearized blob is divided into two or more independent blobs, may determine that a crack occurs in the plate member P.

Referring to FIG. 12B, the analysis unit 150 may extract the outer boundary and the inner boundary of the blob to determine that the crack occurs at the point at which the outer boundary and the inner boundary meet each other.

Through this, the analysis unit may determine whether a crack occurs when the hole H formed on one surface of the plate member P is expanded, and may provide the information on the generation of the crack to the user.

According to the embodiment, the analysis unit 150 may quantitatively derive the size and the hole expansion ratio of the hole H when the crack occurs in the hole H.

In order to verify the reliability of the present disclosure, a hole expansion experiment of the non-plated plate member P was performed according an embodiment of the present disclosure. Accordingly, the size of the hole H of 11.93 mm and the hole expansion ratio of 19.30% were derived. As a result actually measured for the same non-plated plate member P, the size of the hole H of 11.94 mm and the hole expansion ratio of 19.40% were identified. That is, as compared with the result, it were identified that the measurement through the hole expansion ration testing device 100 and the actual measurement have few differences of degrees of 0.08% and 0.52%. Through this, the hole expansion ratio testing device 100 may provide a result of a high reliability as compared with the actual measurement.

Until now, the hole expansion ratio testing method for the non-plated plate member according to the embodiment of the present disclosure has been described with reference to FIGS. 2 to 12B. Hereinafter, the hole expansion ration testing method for a plated plate member will be described through FIGS. 13 to 17B.

FIG. 13 is a flowchart illustrating a hole expansion ratio testing method for a plated plate member according to an embodiment of the present disclosure. FIGS. 14A, 14B, and 14C are pictures illustrating operation S240 according to an embodiment of the present disclosure. FIG. 15 is a flowchart illustrating operation S250 according to an embodiment of the present disclosure. FIGS. 16A and 16B are pictures illustrating operation S253 according to an embodiment of the present disclosure. FIGS. 17A and 17B are pictures illustrating operation S257 according to an embodiment of the present disclosure.

When it is determined that the plate member has been plated, the hole expansion ratio testing device may provide the information of a crack according to the flowchart disclosed in FIG. 13.

Referring to FIG. 13, the hole expansion ratio testing method for a plated plate member may include any one or more of an operation S210 of chucking a plate member having a hole, an operation S220 of expanding the hole, an operation S230 of acquiring an image of the hole, an operation S240 of removing a background of the image, an operation S250 of extracting an interest area for the hole, an operation S260 of linearizing the interest area, and an operation S270 of analyzing a change in a blob in the interest area and providing information on a crack.

Among the operations, the operation S210 of chucking a plate member having a hole, the operation S220 of expanding the hole, the operation S230 of acquiring an image of the hole correspond to the above-described operations S110, S120, and S230, and thus a detailed description thereof will be omitted.

Operation S240

The operation S240 of removing the background of the image is an operation of removing a reflection area of the plated plate member P. Referring to FIG. 14A, in the case of a plated steel plate, when the binarization is performed, a problem of losing a portion of the interest area may occur as in FIG. 14B. The reason why the interest area is lost is that the interest area becomes darker than the surroundings because a portion reflects a larger amount of light than a broken section in the thickness direction of the steel plate due to the plating, and the threshold value increases to an existing value or more due to the reflection of the light in the case of the plated steel plate. Accordingly, in order to extract the interest area, the reflection of the light due to plating should be considered. In order to solve the problem, in the case of the plated plate member P, as in FIG. 14C, a process of removing the reflection area before the binarization process may be further included.

Operation S250

The operation S250 of extracting the interest area of the hole is an operation of extracting the interest area from the image, from which the reflection area has been removed through operation S240. Referring to FIG. 15, the operation S250 of extracting the interest area of the hole may further include any one or more of an operation S251 of dividing the image into a plurality of cells, an operation S253 of binarizing the plurality of unit cells, an operation S255 of detecting a blob by grouping the unit cells for a specific pixel, and an operation S257 of extracting a blob corresponding to the interest area.

Among the operations, the operation S251 of dividing the image into a plurality of cells and the operation S255 of detecting a blob by grouping the unit cells for a specific pixel correspond to the above operations S141 and S145, and thus a detailed description thereof will be omitted.

Operation S253

The operation S253 of binarizing the plurality of unit cells is an operation of binarizing the image divided into the plurality of unit cells. According to the embodiment, the analysis unit 150 may binarize the image, from which the reflection area has been removed through operation S240.

Unlike the embodiment of the present disclosure, when the plate member, from which the reflection area has not been removed, is binarized, as disclosed in FIG. 16A, a portion of the interest area is lost due to the plating of the plate member P, and it is difficult to derive the interest area.

If the image, from which the reflection area has been removed in operation S240, is binarized according to the embodiment of the present disclosure, as illustrated in FIG. 16B, an interest area of a perfect form may be derived. Through this, the analysis unit 150 may distinguish the interest area of the plated plate member P.

Operation S257

Referring back to FIG. 15, the operation S257 of extracting a blob corresponding to the interest area is an operation of extracting the interest area by removing noise of the blob grouped through operation S255. For example, the analysis unit 150 may remove the remaining blobs, except for the blob that is most distant from the center of the image, from the image, from which the blobs corresponding to the background has been removed in operation S147. Referring to FIG. 17A, it can be identified that only a blob that is most distant from the center of the image is left. Through this, the final interest area image disclosed in FIG. 17B may be derived.

According to the embodiment, the analysis unit 150 may quantitatively derive the size and the hole expansion ratio of the hole H when the crack occurs in the hole H.

In order to verify the reliability of the present disclosure, a hole expansion experiment of the plated plate member P was performed according an embodiment of the present disclosure. Accordingly, the size of the hole H of 12.12 mm and the hole expansion ratio of 21.20% were derived. As a result actually measured for the same plated plate member P, the size of the hole H of 12.11 mm and the hole expansion ratio of 21.10% were identified. That is, as compared with the result, it were identified that the measurement through the hole expansion ration testing device 100 and the actual measurement have few differences of degrees of 0.08% and 0.47%. Through this, the hole expansion ratio testing device 100 may provide a result of a high reliability as compared with the actual measurement.

The testing method according to the embodiment of the present disclosure, which has been described with reference to FIGS. 2 to 17B may be implemented by a computer program. Then, the computer program may be executed by the control unit.

Although the preferred embodiments of the present disclosure have been described in detail until now, the scope of the present disclosure is not limited to the embodiments and should be construed by the attached claims. Further, it should be understood that those skilled in the art to which the present disclosure pertains may variously correct and modify the present disclosure without departing from the scope of the present disclosure.

What is claimed is:

1. A hole expansion ratio testing device comprising:
a chucking unit configured to hold a plate member having a hole;
a punching unit inserted into the hole and configured to expand the hole; and
an image acquisition unit configured to acquire an image of the hole expanded by the punching unit; and
an analysis unit configured to extract an interest area corresponding to the hole from the acquired image, linearize the interest area, and provide information on a crack as a blob changes due to the linearization,
wherein the analysis unit extracts the interest area by dividing the image of the acquired hole into a plurality of unit cells, and binarizes the plurality of unit cells by applying independent threshold values for the unit cells.

2. The hole expansion ratio testing device of claim 1, wherein the analysis unit selects a specific pixel from the binarized image, detects blobs by grouping adjacent pixels having the same gray scale as the specific pixel, removes the largest blob from the detected blobs, and provides, among the blobs left after the removal, a blob that is most distant from the center of the image as the interest area.

3. The hole expansion ratio testing device of claim 1, wherein the analysis unit varies a sequence, in which backgrounds are removed from the acquired image, according to whether the plate member is plated.

4. The hole expansion ratio testing device of claim 1, further comprising:
a control unit configured to control the punching unit, wherein, when it is determined through the analysis unit that there is a crack in the plate member, the control unit controls the punching unit to stop the movement of the punching unit, and the analysis unit derives a size and a hole expansion ratio of the hole in a state in which the punching unit is stopped.

5. The hole expansion ratio testing device of claim 1, wherein the analysis unit linearizes the extracted interest area with reference to an arbitrary point.

6. The hole expansion ratio testing device of claim 1, wherein the analysis unit provides information on the crack according to the numbers of the blobs before and after the linearization of the interest area.

7. The hole expansion ratio testing device of claim 1, wherein the analysis unit provides information on the crack according to whether an outer boundary and an inner boundary of the blob in the interest area meet each other after the linearization.

8. A hole expansion ratio testing device comprising:
a chucking unit configured to hold a plate member having a hole;
a punching unit inserted into the hole and configured to expand the hole;
an image acquisition unit configured to acquire an image of the hole expanded by the punching unit; and
an analysis unit configured to extract an interest area corresponding to the hole from the acquired image, linearize the interest area, and provide information on a crack as a blob changes due to the linearization,
wherein the analysis unit varies a sequence, in which backgrounds are removed from the acquired image, according to whether the plate member is plated,
wherein when the plate member is plated, the analysis unit removes a background defined as an area reflected due to the plating, and extracts the interest area from the image, from which the background has been removed.

9. The hole expansion ratio testing device of claim 8, wherein the analysis unit selects a specific pixel from the binarized image, detects blobs by grouping adjacent pixels having the same gray scale as the specific pixel, removes the largest blob from the detected blobs, and provides a blob that is most distant from the center of the image as the interest area.

10. A hole expansion ratio testing method comprising:
holding a plate member having a hole;
expanding the hole by inserting the punching unit into the interior of the hole;
acquiring an image of the hole while the hole is expanded;
extracting an interest area corresponding to the hole from the acquired image;
linearizing the interest area; and
providing information on a crack as a blob changes due to the linearization, and
determining whether the plate member has been plated,
wherein the extracting of the interest area comprises, when it is determined that the plate member has not been plated, removing a background of the image, and
wherein the hole expansion ratio testing method further comprises, when it is determined that the plate member has been plated, removing the background of the image, before the extracting of the interest area.

11. The hole expansion ratio testing method of claim 10, wherein the providing of the information on the crack comprises:
considering at least one of information on the numbers of the blobs before and after the linearization of the interest area and information on whether an outer boundary and an inner boundary of the blob in the interest area meet each other after the linearization.

12. A hole expansion ratio testing method comprising:
holding a plate member having a hole;
expanding the hole by inserting the punching unit into the interior of the hole;
acquiring an image of the hole while the hole is expanded;
extracting an interest area corresponding to the hole from the acquired image;
linearizing the interest area; and
providing information on a crack as a blob changes due to the linearization,
wherein the extracting of the interest area comprises:
when the plate member has not been plated,
selecting a specific pixel from the binarized image, and detecting blobs by grouping adjacent pixels having the same gray scale as the specific pixel; and
removing the largest blob from the detected blobs, and providing, among the blobs left after the removal, a blob that is most distant from the center of the image as the interest area, and
when the plate member has been plated,
selecting a specific pixel from the binarized image, and detecting blobs by grouping adjacent pixels having the same gray scale as the specific pixel; and
providing a blob that is most distance from the center of the image as the interest area.

13. A hole expansion ratio testing program stored in a medium to execute operations of:
holding a plate member having a hole;
expanding the hole by inserting the punching unit into the interior of the hole;
acquiring an image of the hole while the hole is expanded;
extracting an interest area corresponding to the hole from the acquired image;
linearizing the interest area;
providing information on a crack as a blob changes due to the linearization; and
determining whether the plate member has been plated,
wherein the extracting of the interest area comprises:
when it is determined that the plate member has not been plated, removing a background of the image, and
wherein the hole expansion ratio testing method further comprises, when it is determined that the plate member has been plated, removing the background of the image, before the extracting of the interest area.

* * * * *